United States Patent
Steinberg (10) Patent No.: US 7,434,584 B2
(45) Date of Patent: Oct. 14, 2008

(54) VAPORIZATION PIPE WITH FLAME FILTER

(75) Inventor: Dan Steinberg, Blacksburg, VA (US)

(73) Assignee: VaporGenie, LLC, Blackburg, VA (US)

( * ) Notice: Subject to any disclaimer, the term of this patent is extended or adjusted under 35 U.S.C. 154(b) by 246 days.

(21) Appl. No.: 10/639,344

(22) Filed: Aug. 12, 2003

(65) Prior Publication Data

US 2004/0031495 A1 Feb. 19, 2004

Related U.S. Application Data

(63) Continuation-in-part of application No. 10/318,877, filed on Dec. 13, 2002, now abandoned.

(60) Provisional application No. 60/366,809, filed on Mar. 22, 2002, provisional application No. 60/384,551, filed on May 29, 2002, provisional application No. 60/399,465, filed on Jul. 29, 2002, provisional application No. 60/429,120, filed on Nov. 26, 2002.

(51) Int. Cl.
*A24F 1/00* (2006.01)
*A24F 47/00* (2006.01)
(52) U.S. Cl. .................... 131/194; 131/196; 131/271
(58) Field of Classification Search ................ 131/194, 131/196, 226, 174; 128/202.21; D27/163, D27/165
See application file for complete search history.

(56) References Cited

U.S. PATENT DOCUMENTS

| | | | | | |
|---|---|---|---|---|---|
| 1,743,698 | A | * | 1/1930 | Walker | 131/331 |
| 2,459,670 | A | * | 1/1949 | Morris | 131/184.2 |
| 2,770,241 | A | * | 11/1956 | Winkler | 131/332 |
| 3,939,849 | A | * | 2/1976 | Baxter et al. | 131/332 |
| 4,020,853 | A | * | 5/1977 | Nuttall | 131/195 |
| 4,224,953 | A | * | 9/1980 | Alvarez | 131/179 |
| 4,407,967 | A | * | 10/1983 | Luks | 501/81 |
| 4,713,180 | A | * | 12/1987 | Hofmann et al. | 75/407 |
| 5,657,772 | A | * | 8/1997 | Duke et al. | 131/334 |
| 6,077,620 | A | * | 6/2000 | Pettit | 429/26 |
| 6,095,153 | A | * | 8/2000 | Kessler et al. | 131/194 |
| 6,354,301 | B2 | * | 3/2002 | McCoy | 131/194 |
| 6,444,006 | B1 | * | 9/2002 | Haberkamp et al. | 55/521 |
| 6,536,442 | B2 | * | 3/2003 | St. Charles et al. | 131/194 |
| 6,715,494 | B1 | * | 4/2004 | McCoy | 131/194 |

OTHER PUBLICATIONS www.wikipedia.com (website last updated on Sep. 23, 2004 per www.archive.org).*
Merriam-Webster's Online Dictionary (www.m-w.com) (website last updated on Nov. 30, 2004 per www.archive.org).*

* cited by examiner

*Primary Examiner*—Philip C Tucker
*Assistant Examiner*—Michael J Felton (57) ABSTRACT

A vaporizer device that uses a flame for vaporizing flavor and psychoactive compounds from smoking materials such as tobacco. The present device has a filter unit 34 with a porous flame filter 36. The flame filter 36 can be made of open-cell ceramic or metal foam, sintered ceramic or metal granules or other porous, heat resistant materials. In use, flame is supplied to the flame filter, and inhalation causes ambient air to enter the flame filter as well. The flame exhaust and ambient air are mixed within the flame filter and produce an air stream of intermediate temperature. The intermediate temperature air stream is hot enough to vaporize desirable components from the smoking material, but generally is not hot enough to burn the smoking material. The temperature of the air stream can be controlled by adjusting the amount of flame supplied to the flame filter 36.

32 Claims, 7 Drawing Sheets

Fig. 14 low temp
Fig. 15a high temp
Fig. 15b

VAPORIZATION PIPE WITH FLAME FILTER

RELATED APPLICATIONS

The present application is a continuation-in-part of copending patent application Ser. No. 10/318,877, filed on Dec. 13, 2002 (now abandoned), which claims the benefit of priority from the following copending provisional patent applications: 60/366,809 filed on Mar. 22, 2002; 60/384,551 filed on May 29, 2002; 60/399,465 filed on Jul. 29, 2002; and 60/429,120 filed on Nov. 26, 2002

FIELD OF THE INVENTION

The present invention relates generally to smoking devices and vaporization devices. More particularly, the present invention relates to a pipe designed to provide vaporization by using heat from a flame.

BACKGROUND OF THE INVENTION

Tobacco, kinnick kinnick, or other herbs are typically smoked by burning and inhaling the combustion fumes and smoke. In recent years, interest has grown in the technique of vaporization in which the smoking material is carefully heated so that the desired flavor and psychoactive components are liberated, and combustion is minimized.

Vaporization provides many benefits over smoking. When performed properly, vaporization does not produce nearly as much toxic and carcinogenic pyrolytic products as smoking. Also, vaporization is smoother and more flavorful, and lacks a burned taste that many find disagreeable. Further, vaporization allows more efficient use of smoking materials, since desired flavor and psychoactive compounds are not destroyed by combustion.

However, vaporization is difficult to perform, since vaporization only occurs in a relatively narrow temperature range. If the temperature is too low, desired compounds are not volatilized and nothing is inhaled; if the temperature is too high, combustion will occur, with its ill effects. For most smoking materials, vaporization is optimal in a temperature range of about 300-400 degrees Fahrenheit. The optimal temperature depends upon the compounds being vaporized.

Most vaporizers in use today are electrically powered. For vaporizing plant materials such as tobacco or essential oils, a temperature-controlled heat gun is often used. Electrical vaporization devices are inconvenient to use since they are not portable and require electrical line power. Typically, heat guns require several hundred watts of power. Also, electrical vaporization devices tend to be expensive.

Some vaporizer devices employ a burning carbonaceous fuel element as a heat source. These devices are best suited for use in cigarettes since the carbonaceous fuel element burns for several minutes. However, a continuously burning fuel element is not desired for vaporizing some materials. Exemplary vaporizer devices in the prior art are listed below:

U.S. Pat. No. 4,219,032 describes a smoking device using a fuel element.

U.S. Pat. No. 5,993,748 describes a vaporization device that is electrically powered.

U.S. Pat. No. 4,141,369 describes a vaporization device that is electrically powered.

U.S. Pat. No. 6,354,301 describes a vaporizer attachment for a pipe so that the pipe can be coupled to an electric heat gun.

U.S. Pat. No. 4,303,083 describes a vaporizer that is electrically powered.

It would be an advance in the art of vaporization devices to provide a vaporizer that operates without electrical power, is inexpensive, is easily transportable, is small, and is simple to operate. Such a device could be widely used by tobacco smokers and by users of medicinal herbs (e.g. mullein, kinnick kinnick) and essential oils. Such a device would also largely avoid the harmful effects of inhaling toxic pyrolytic compounds found in smoke and provide the other benefits of vaporization.

SUMMARY

The present invention includes a vaporization device having a pipe with a bowl for holding smoking material (e.g. tobacco or other medicinal plant-based materials), and a heat resistant and porous flame filter for receiving a flame, wherein the flame filter has a thickness of at least 0.02 inches. The flame filter can also have thickness of at least 0.1 inch, or in the range of 0.125-1 inches. In one embodiment, the flame filter is made of open cell ceramic foam, which can comprise silicon carbide, silicon, cordierite or other ceramics. The flame filter causes mixing between flame exhaust and ambient air.

The flame filter can also be made of bonded granules (e.g. sintered metal or ceramic granules), stacked discs (with each disc having at least one hole), a tangled lump of metal wire, or stacked screens, for example. Generally, the flame filter material should have a thermal conductivity of at least 30 W/mK. The pipe can also have an airflow shutter to automatically regulate the amount of airflow into the flame filter, and thereby regulate the temperature. The device can also have a means for indicating temperature, such as an electronic temperature sensor with a display, or a bimetallic strip that moves in response to temperature.

In one useful embodiment, the flame filter comprises open cell silicon carbide foam made by chemical vapor deposition. The foam can have about 40-120 or 60-100 pores-per-inch (PPI), for example.

The present invention also may have a filter housing for holding the flame filter. The filter housing can be made of thermally insulating material (e.g. wood) so that a user is protected from touching the hot flame filter. The filter housing can also be hollow to provide thermal insulation.

The present invention also includes a filter unit having a filter housing, a flame filter disposed in the housing, and a means for attaching the filter housing to a pipe. The filter unit of the present invention can be used with many different kinds and styles of smoking pipes and will transform conventional smoking pipe into a vaporization pipe. The means for attaching the pipe can be a threaded connection, magnet, clamp, hinge and the like.

DETAILED DESCRIPTION

The present invention provides a vaporizing pipe that vaporizes flavor compounds, medicinal compounds and psychoactive compounds from smoking material such as tobacco, mullein, passion flower, cloves, yohimbe, mint, tea, eucalyptus, chamomile and the like. Many of these plant materials have medicinal compounds that can be inhaled when vaporized. The present vaporizer pipe can be used with a flame such as from a conventional butane lighter or a match. The vaporization pipe of the present invention has a heat resistant, porous flame filter disposed upstream from the smoking material. In operation, flame exhaust and ambient air are drawn into the flame filter. The flame filter causes mixing between the flame exhaust and ambient air, and also conducts heat between the flame exhaust and ambient air. The flame filter thereby creates an intermediate temperature (e.g. about 300-400 F.) air stream capable of vaporizing without burning. The smoking material is in the path of the intermediate temperature air stream, and so volatile flavor and psychoactive compounds are vaporized from the smoking material. The intermediate temperature air stream and vaporized compounds are then inhaled. The flame filter can be made of many heat-resistant materials such as metals (e.g. refractory metals, noble metals), ceramics and the like. The material of the flame filter should be resistant to oxidation at high temperature, resistant to cracking under extreme thermal shock, and have a high thermal conductivity. In preferred embodiments of the invention, the flame filter comprises open-cell ceramic foam.

Definitions:

Heat resistant: Capable of not melting and maintaining its physical structure when exposed to heat from a small flame. Materials that oxidize slightly when exposed to flame (e.g. bronze, stainless steel) are considered heat resistant in the invention. However, combustible materials (e.g. carbon) are not heat resistant.

Porous: Having flow paths that create mixing of flame exhaust and air.

Figure 1:
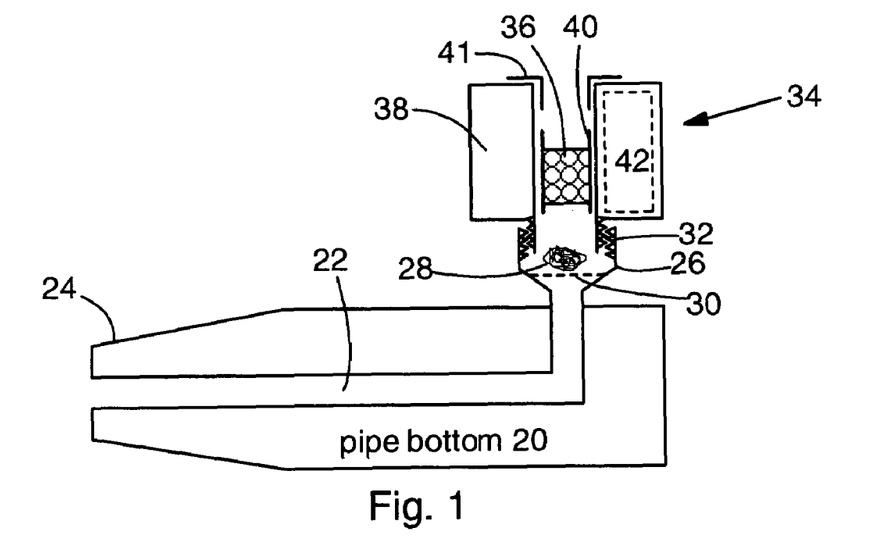
FIG. 1 shows a cross-sectional side view of a vaporization pipe according to the present invention.

FIG. 1 is a cross sectional side view of the present vaporization pipe. The pipe has a pipe bottom 20 having a hole 22 through which vapor is inhaled. The pipe has an inhalation end 24 for contact with a users mouth during use. The pipe also has a bowl 26 for holding smoking material 28, such as tobacco or other herbs or essential oils. The bowl 26 preferably has a mesh screen 30 for supporting the smoking material. A filter unit 34 is removably attached to the bowl 26 by threaded connection 32. The filter unit 34 has a heat-resistant and porous flame filter 36 and a filter housing 38 surrounding the flame filter 36. The filter unit 34 may optionally have a heat shield 40 disposed between the filter housing 38 and the flame filter 36. The heat shield 40 can be a thin sheet (e.g. 0.002" thick) of stainless steel foil, for example. A corner heat shield 41 can also be provided at an opening in the filter housing 38. The corner heat shield 41 and heat shield can comprise a single component. The corner heat shield 41 helps protect the filter housing 38 from flame. The filter unit 34 may make an airtight seal with the bowl 26, but an airtight seal is not absolutely required in the invention; a small amount of air leakage is permissible.

If essential oils are used, the smoking material can comprise glass or stainless steel wool, or ceramic foam or paper with the oil absorbed therein. The wool or foam will function as an inert carrier and will allow the essential oil to vaporize without dripping down into the pipe.

The pipe bottom 20 and filter housing 38 can be made of many different materials such as wood, glass, ceramic, metal or the like. Materials with low thermal conductivity such as wood are generally preferred, but not required in the invention. The filter housing 38 should also be made of a material with low thermal conductivity so that heat from the flame filter 36 does not escape to the exterior surfaces. The filter housing 38 can be made of wood, closed-cell ceramic foam, metal or the like. Alternatively, the filter housing has a hollow space 42 to provide low thermal conductivity. The pipe bottom 20 can also have a hollow space (not shown) for thermal insulation. The bowl 26 can be made of metal (e.g., stainless steel or brass), in which case it maybe plated with a relatively chemically nonreactive metal such as silver, gold, platinum or chromium.

The present invention necessarily includes the porous flame filter 36. The flame filter is made of heat resistant material such as ceramic or metal (e.g. refractory metal). The flame filter is made of porous material. The flame filter can be made of many structures, such as open cell foam (ceramic or metal), sintered or bonded ceramic or metal granules, stacked ceramic or metal screens or porous plates, coils or tangled lengths of wire, or stacked discs with holes. If plates are used, the plates can each have many holes or a single hole. A stack of plates with holes or a hole is considered to be porous in the invention, even if the plates are made of nonporous material.

Figure 2:
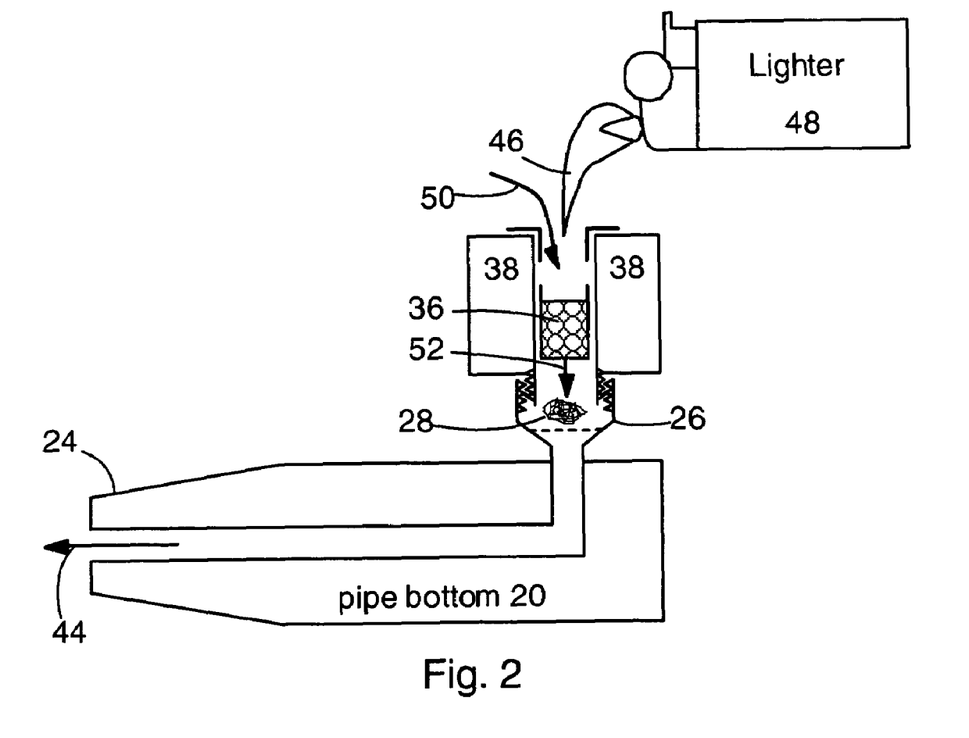
FIG. 2 illustrates the present vaporization pipe in operation.

FIG. 2 shows the pipe of the present invention in operation. In operation, smoking material 28 is disposed in the bowl, and a user (not shown) inhales air and vaporization products from the inhalation end 24, as indicated by arrow 44. Flame 46 is provided to the flame filter 36 by a lighter 48 or other flame source, such as a match. The flame may or may not touch the flame filter, but it is best for the flame to be held slightly above the flame filter 36. Hot exhaust from the flame 46 is drawn into the flame filter 36. Cold, ambient air 50 is also drawn into the flame filter. The flame filter 36 causes mixing and heat exchange between the flame exhaust and ambient air. The flame exhaust and ambient air, after mixing and exchanging heat in the filter 36, form an intermediate-temperature air stream 52 that flows through the smoking material. The intermediate-temperature air stream 52 can have a temperature of about 250-500 degrees Fahrenheit, depending on a number of factors such as the speed of inhalation, the size and temperature of the flame 46, and the temperature of the ambient air.

More typically, the temperature of the air stream 52 will be about 275-400 F. By controlling the application of flame to the flame filter 36 (e.g. lifting or lowering the lighter), the speed of inhalation, and the size of the flame, a user can modulate the temperature of the air stream 52. With experience, a user can determine the temperature by taste and mouth sensations, and adjust the amount of flame accordingly to obtain a perfect temperature for vaporization.

Preferably in the invention, the flame filter 36 and bowl 26 are located so that the intermediate temperature air stream 52 flows straight through the smoking material. For example, in FIG. 2, the airflow path from the filter 36 to the pipe bottom 20 extends in a straight line through the smoking material 28. Forcing hot air to flow through the smoking material 28 increases vaporization of compounds from the smoking material.

Figure 3:
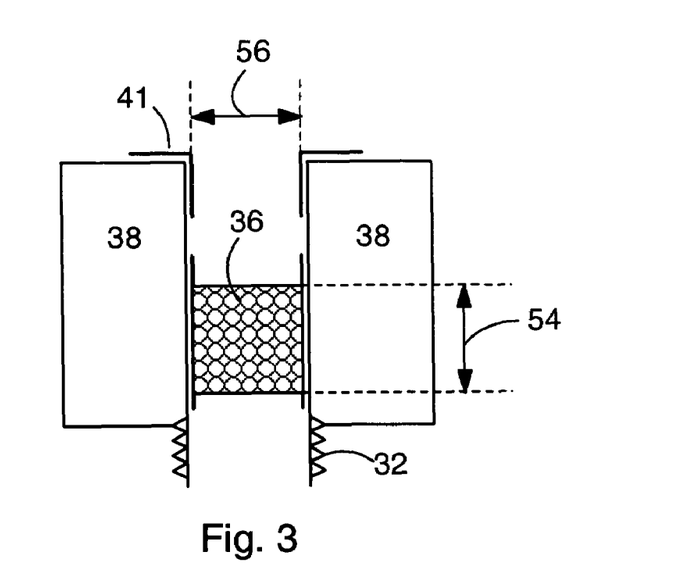
FIG. 3 shows a close-up of a filter unit according to the present invention.

FIG. 3 shows a close-up view of the filter unit 34 of the present invention. The flame filter 36 has a thickness 54, which is measured in the direction of airflow through the filter 36. In the present invention, the flame filter 36 must have a thickness 54 of at least 0.02 inches. A thickness of 0.02 inches is the absolute minimum required for at least partially adequate mixing and heat exchange between the flame exhaust and ambient air. If the filter is thinner than 0.02 inches, then the flame will tend to burn the smoking material. More preferably, the flame filter has a thickness of at least 0.05 inches, 0.1 inches, 0.125 inches or 0.2 inches. A thicker flame filter provides more even heating of the smoking material, and tends to provide lower temperatures. The flame filter will typically have a thickness in the range of about 0.25-0.75 inches, but the thickness of the filter can also be as great as 1 or 2 inches or greater in the invention. The thickness of the filter will depend somewhat on the amount of mixing provided by the filter structure (e.g. pore sizes), and the thermal conductivity of the filter material. High mixing capability (e.g. small pore size, and a reticulated structure) and high thermal conductivity will allow for a thinner filter. Thicker filters are required if the pore size is large (e.g. 0.1 inch), and the filter has a low thermal conductivity (e.g. below 10 W/mK)

The flame filter 36 may be cylindrically shaped (although it is not necessarily cylindrical), with a diameter 56. The diameter may be selected to be within the range of about 0.125-1.0 inches (i.e. cross sectional area of about 0.015 square inch to about 1 square inch). The present invention includes embodiments where the flame filter is larger or smaller than this range. In one embodiment, the cross sectional area is about 0.1 to about 0.5 square inches. The present invention also includes embodiments where the flame filter is square, rectangular or any other shape in cross-section.

The porous flame filter 36 is essential in the invention. The flame filter 36 can be made of many different materials and structures, all of which are understood to be included in the invention and within the scope of the appended claims. Materials and structures suitable for the flame filter include:

Bonded granules—In this embodiment, the flame filter is made of granules of heat resistant materials bonded or sintered together. Examples include sintered bronze, brass, stainless steel, or other metals. Also included are sintered ceramics such as alumina, cordierite, or porcelain. Bonded silicon carbide granules can be used as well. The granules can have sizes in the range of about 100-2000 microns, for example. If metals are used, a chemically stable coating (e.g. gold or platinum) can be applied to prevent oxidation. The porosity (volume % of open space) should be relatively high, for example at least 20 or 30%. The pore size should be relatively large so that one can inhale easily; for example, the pore size can be about 100-1000 microns.

Stack of plates or screens—The flame filter can comprise a stack of at least two, preferably at least three or four metal screens. For example, conventional metal screens can be used. In this case, the metal should have a relatively high thermal conductivity above about 30 W/mK (e.g. brass or silver). Also, the metal may be resistant to oxidation, or have a protective coating (e.g. gold or platinum). Alternatively, the flame filter can comprise a stack of at least two, preferably at least three or four ceramic or metal plates with holes. A series of plates with holes is considered to be 'porous' in the present invention and appended claims.

Metal wire—The flame filter can also comprise a web of metal wire (e.g. 20-30 gauge). The metal may be resistant to oxidation or have a protective coating (e.g. platinum or gold), and have a high thermal conductivity (e.g. copper, brass or silver). The metal wire can be tangled, coiled, folded or in any other configuration that creates mixing of air and flame exhaust and provides heat exchange. The metal wire can have a round cross-sectional shape, or can be flat ribbon.

Reticulated open-cell foam—The flame filter can also comprise open cell metal or ceramic foam. In this case, the foam can have a pores-per-inch (PPI) rating of about 30-120, more preferably in the range of 50-100 PPI, inclusive. If metal is used, it should be heat resistant, and possibly coated with a protective coating (e.g. gold, platinum or other platinum-family metals). If ceramic is used, the foam can be made by applying a ceramic slurry to a burnable (e.g. urethane) foam substrate, and then kiln-firing, as known in the art. Also, the ceramic foam can be made by chemical vapor deposition (CVD) onto a foam substrate, also as known in the art. If CVD ceramic foam is used, it can be made of silicon carbide, which has very high oxidation resistance and thermal shock capability, is relatively inert, and has high thermal conductivity, which are all desirable properties. CVD ceramic foam can also be made of silicon, which also has high thermal conductivity and heat resistance. Other possible materials for the ceramic foam include cordierite, zirconium-containing ceramics, or silica-containing ceramics, or combinations of these materials. Some ceramic materials may break apart or crack due to the thermal shock of the applied flame, which is undesirable. Hence, a ceramic material should be selected that can withstand the thermal shock. A particularly useful material for the flame filter is 80 PPI CVD silicon carbide open-cell foam. The foam may have a relative density (volume occupied by solid material) of about 5-25% or about 8-12%. It is also noted that not all of the cells need to be open; some cells can be closed, as often occurs in ceramic foam made from slurry applied to polymer foam.

Most generally, the flame filter can comprise any heat-resistant, porous material that causes mixing of and heat exchange between of the flame exhaust and air, and has a thickness of at least 0.05 inches, or 0.1 inches. Reticulated structures such as open cell foams are preferred, but the invention and appended claims include all the materials listed above. The flame filter should resist melting up to at least the temperature of the flame of course, and preferably resists oxidation up to about 1000 degrees Fahrenheit. Some oxidation is acceptable if it forms a protective coating. Also, the material of the flame filter (i.e. not including pore spaces), may have a thermal conductivity of at least 30 W/mK. Silicon carbide can have thermal conductivity of about 120 W/mK, and so provides good heat transfer. A high thermal conductivity facilitates heat transfer between the flame exhaust and ambient air, thereby ensuring that the intermediate temperature air stream has a uniform temperature.

The flame filter can have a protective coating (e.g. platinum) to protect it from oxidation and chemical reactions. A protective coating can be particularly useful in embodiments employing metals, such as metal wire or sintered metal granules.

It is also noted that the flame filter 36 can have a combustion catalytic coating (e.g. platinum or palladium or a combination thereof) for causing more complete combustion of the flame exhaust. This will tend to reduce the amount of harmful combustion products inhaled from the flame.

Also, it is noted that the filter can include means (e.g. threads, friction fit) for direct attachment to the pipe. Preferably, the flame filter is disposed in a filter housing, because the flame filter typically gets too hot to safely handle directly. If a filter housing is used, the flame filter can be attached to the pipe indirectly through the filter housing. It is understood that the flame filter is considered attached to the pipe even in embodiments where the flame filter is directly attached only to the filter housing.

It is noted that the filter unit 34 can attach to the pipe with many different mechanisms. Examples include magnetized components that attach by magnetic attraction, screw threads as shown in FIGS. 1 and 2, friction fit (with or without O-rings) hinges, springed clamps and the like.

It is noted that it is preferable for the bowl to be constructed such that air flows in a straight path through the smoking material (as in all the pipes shown). In other words, the air preferably exits the bottom of the bowl, opposite the filter. This tends to result in all the smoking material being exposed to the hot airflow. In some conventional pipes (e.g. large conventional tobacco pipes), by contrast, the bowl is constructed so that air exits the side of the bowl, thus requiring that the hot air make a 90-degree turn within the bowl. This tends to result in unvaporized smoking material on the side of the bowl furthest from the bowl exit, which is undesirable.

Figure 4A:
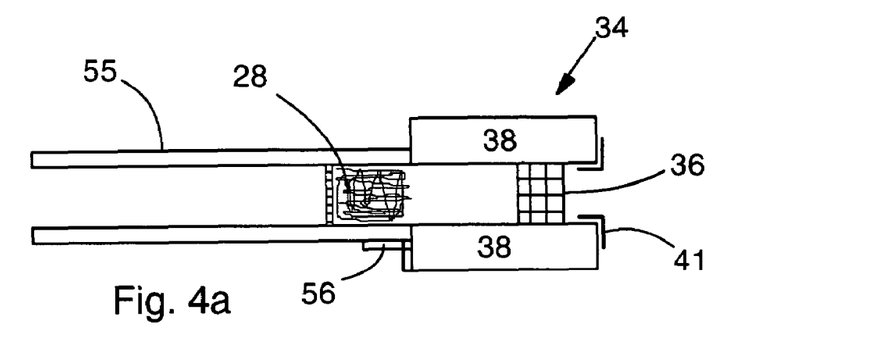
FIGS. 4a and 4b show an alternative embodiment of the invention having a hinged filter unit, and a straight pipe.
Figure 4B:
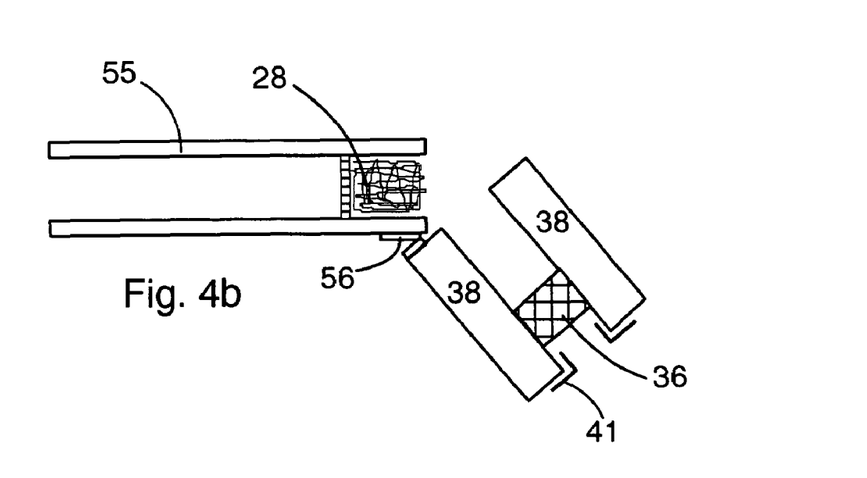

FIGS. 4a and 4b illustrate an alternative embodiment of the invention where the filter unit 34 is attached to a straight pipe 55 with a hinge 56. The hinge allows the smoking material 28 to be inserted, and removed when it is spent. It is understood that a hinge attachment is considered to be an example of a 'removable' attachment in the present invention and appended claims.

Figure 5:
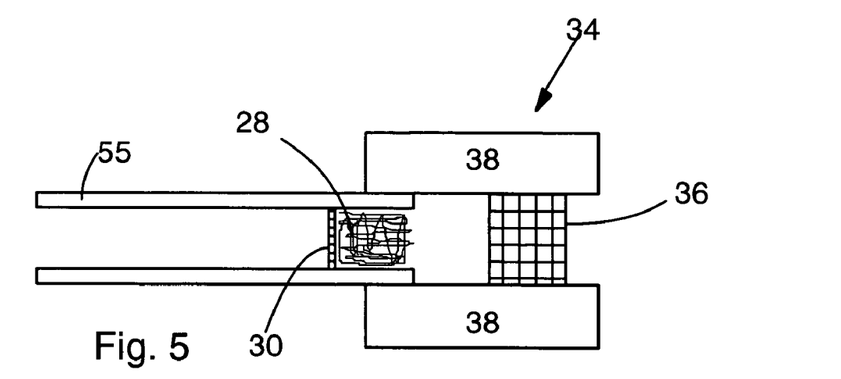
FIG. 5 shows an alternative embodiment of the invention having a friction-fit filter unit.

FIG. 5 shows an alternative embodiment where the filter unit 34 is attached to the straight pipe by sliding over the straight pipe 55 with a friction fit. An O-ring (not shown) can be disposed between the filter housing 38 and the straight pipe 55.

Figure 6:
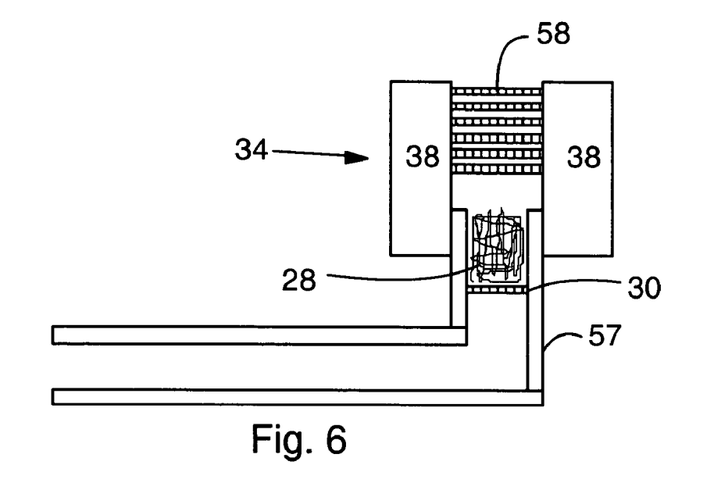
FIG. 6 shows an embodiment wherein the flame filter is a stack of screens (metal or ceramic).

FIG. 6 shows an embodiment of the invention having a stack of 6 screens 58 as the flame filter. The screens can be made of metal mesh, for example, or ceramic. The filter unit 34 fits onto a pipe 57 with a friction fit, for example. The screens 58 may be spaced apart as shown, or may be in contact. A series of screens is considered to be 'porous' in the invention.

Figure 7:
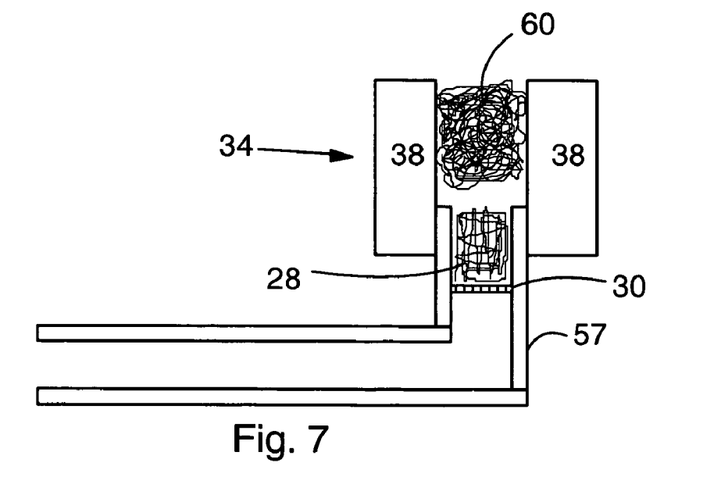
FIG. 7 shows an embodiment wherein the flame filter is a tangled web of wire.

FIG. 7 shows an embodiment where the flame filter comprises a web of metal wire 60. The wire can be 20-30 gauge, for example, and can be round or flat. The wire can be tangled, as shown, or can be coiled or folded in an organized fashion.

Figure 8:
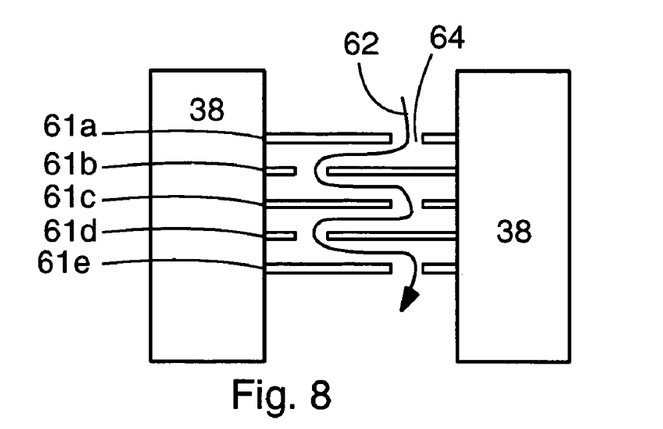
FIG. 8 shows a close-up of the filter unit where the flame filter comprises a stack of 5 discs with holes.

FIG. 8 shows a close-up of the filter unit 34 in an embodiment where the porous flame filter comprises a series of 5 discs 61a-61e, with each disc having holes 64. The discs can be made of metal or ceramic or any other heat-resistant material, for example. The discs have holes in different locations, so that ambient air and flame exhaust follow a tortured path 62. The tortured path creates mixing between the flame exhaust and the ambient air, as required in the present invention. The disc material may or may not be porous, but the combination of stacked discs is considered porous in the invention. The number is discs can be in the range of about 3-20, for example. Each disc can have one or more holes.

Figure 9:
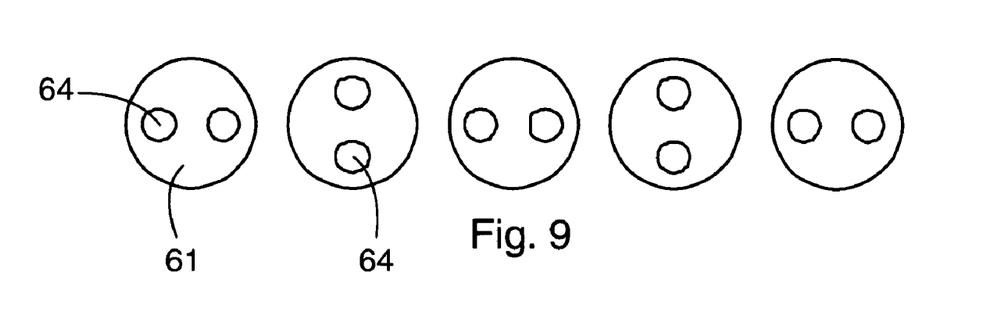
FIGS. 9 and 10 show top view of exemplary discs possible in the embodiment of FIG. 9.
Figure 10:
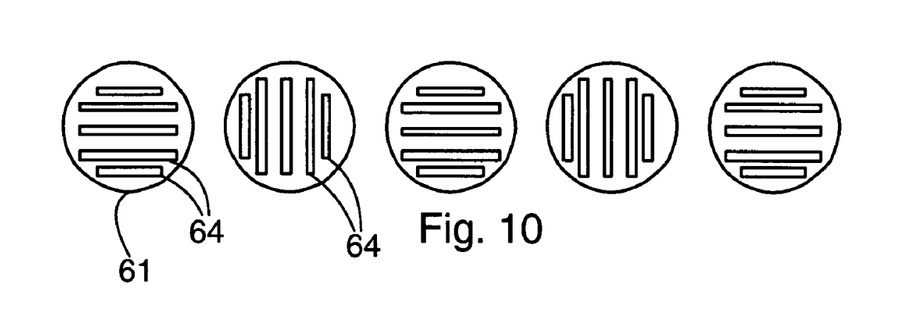

FIG. 9a shows a group of 5 discs that can be used in the embodiment of FIG. 8. Each disc has the same hole pattern, but each disc is rotated so that the holes in adjacent discs are not overlapping. This assures that the flame exhaust and ambient air follow a tortured path and are mixed as they pass between the discs. FIG. 10 shows an alternative group of discs 61 having elongated holes 64 arranged in a striped pattern. The discs can be round (as shown), or square, rectangular or any other shape. The discs can have a wide range of thicknesses.

Figure 11:
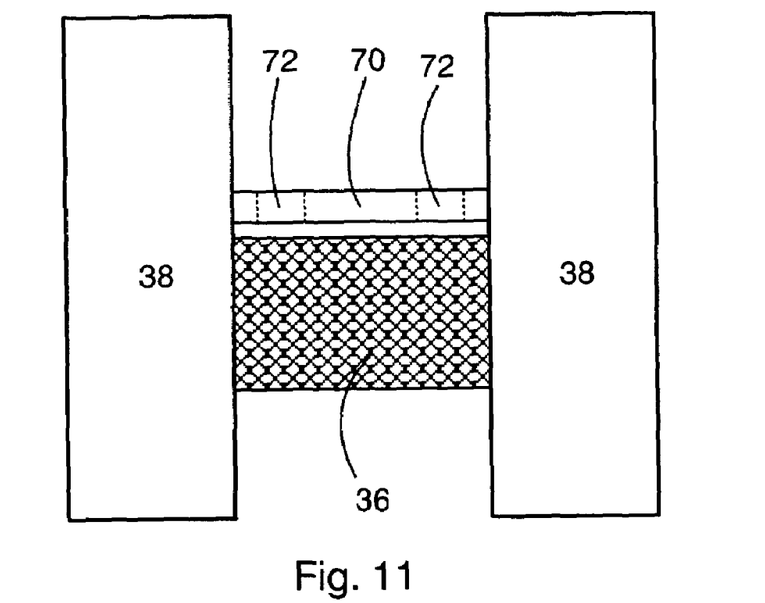
FIG. 11 shows a close-up of the filter unit where the flame filter is combined with a disc having holes that directs heat to the periphery of the flame filter.
Figures 12, 13:
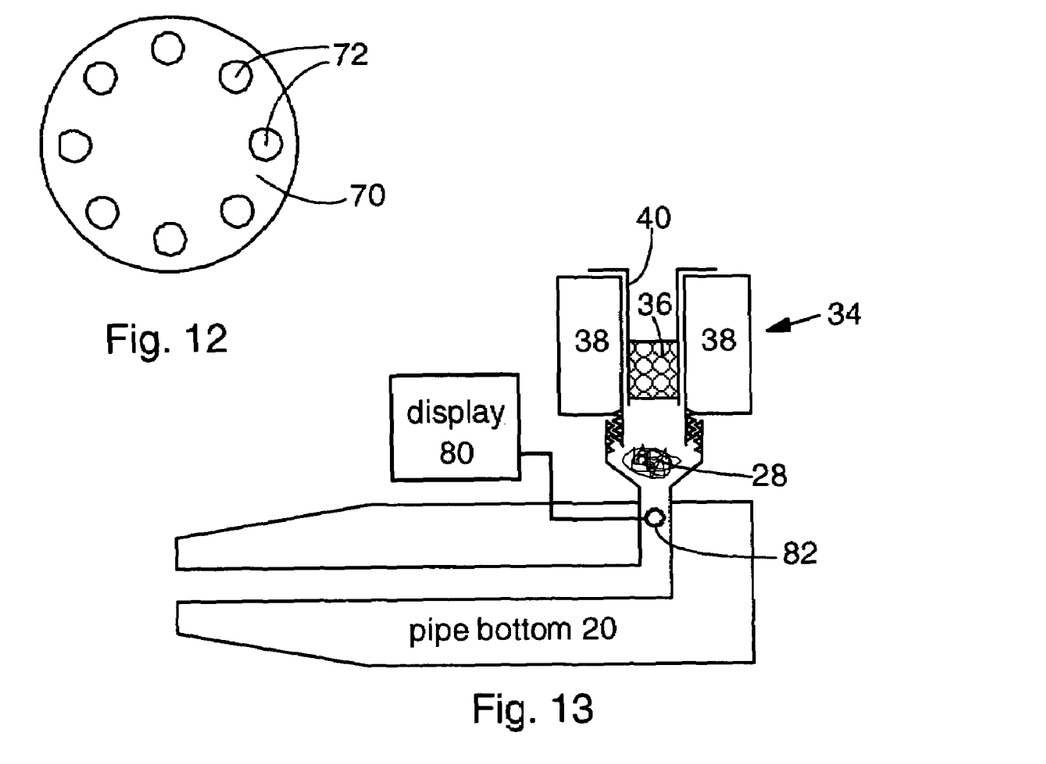
FIG. 12 is a top view of an exemplary disc that can be used in the embodiment of FIG. 11.
FIG. 13 shows an embodiment having an electronic temperature sensor and temperature display.

FIG. 11 shows yet another embodiment of the filter unit 34 wherein the flame filter 36 is combined with a disc 70 over the flame filter 36. The disc 70 has holes 72 around the periphery. The holes 72 are located at the periphery, and so tend to direct heat toward the periphery of the filter, and thereby create a more uniform heat distribution in the smoking material. Without the disc 70, sometimes the temperature can be too hot in the center, and too low at the edges. FIG. 12 shows a top view of the disc. The disc can have any number of holes (e.g. 3-10), and the holes can be any shape. The disc 70 can also be located under (on the downstream side of) the flame filter 36. The embodiment of FIGS. 11 and 12 is most useful where the flame filter 36 comprises a reticulated structure such as foam or bonded granules. In an alternative embodiment, the disc 70 has no holes, and has a smaller diameter than the flame filter 36, so that it directs airflow to the periphery. The disc 70 can be bonded to the flame filter 36.

FIG. 13 shows another embodiment having an electronic temperature indicator 80 coupled to a temperature sensor 82 such as a thermistor or thermocouple. The temperature sensor 82 should be located close to the smoking material 28. The temperature sensor can be located behind (downstream from) the smoking material, as shown, or can be located between the flame filter 36 and the smoking material 28. In operation, the display 80 provide the user with an indication of the temperature at the smoking material. This is useful for some users who have difficultly adjusting the flame application to achieve the best vaporization temperature. The display may have an LED, or liquid crystal element to indicate an approximate temperature to the user, for example with a bar display. By using the display, the user can more accurately adjust the temperature inside the smoking material 28.

Figure 14:
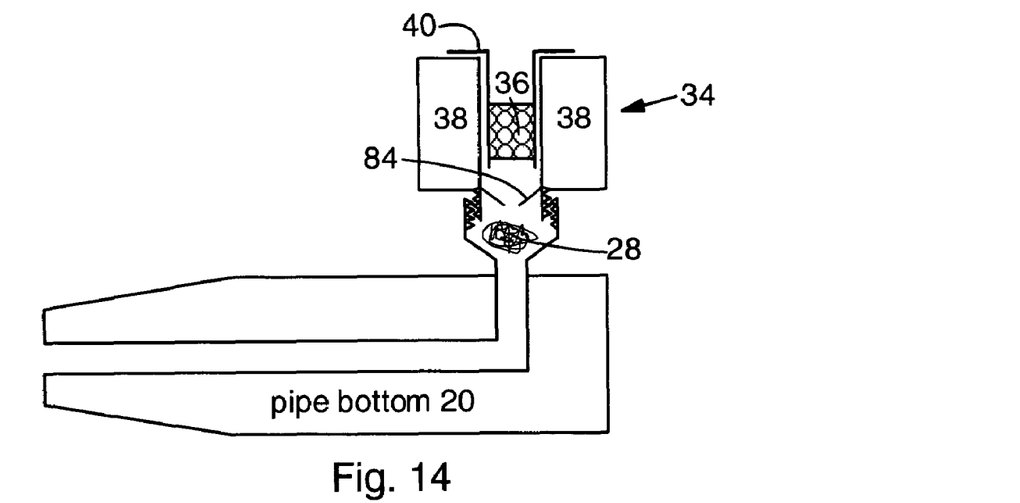
FIG. 14 shows an embodiment having a mechanical airflow shutter responsive to temperature for regulating temperature.
Figure 15A:
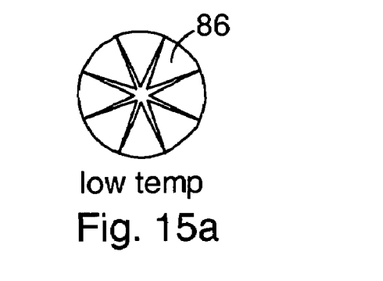
FIGS. 15a and 15b show top views of an exemplary airflow shutter usable in the embodiment of FIG. 14.
Figure 15B:
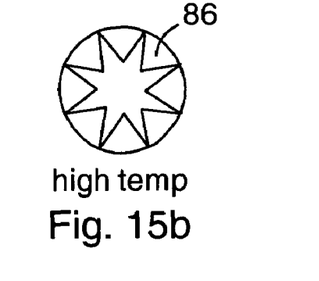

FIG. 14 shows another aspect of the invention wherein the pipe includes a thermo-mechanical airflow shutter 84 for controlling airflow in response to temperature. In the present vaporization pipe, the amount of airflow influences the temperature at the smoking material. Specifically, for a constant flame size, higher airflow (stronger inhalation) results in cooler temperature, since higher airflow requires more ambient air. Hence, the thermomechanical shutter 84 can maintain a somewhat constant temperature by restricting airflow when temperature is too low. More specifically, the shutter 84 opens when is it exposed to excessive temperature (e.g. temperatures that can cause burning), thereby allowing more ambient air, and reducing the temperature. The shutter can be made of a bimetallic strip partially blocking the air passage. When exposed to high temperature, the shutter 84 bends to open the airway. Many different shapes and structures can be used for the shutter 84. FIGS. 15a and 15b, for example, show top views of a shutter made of bimetallic sheet at low and high temperature, respectively. Leaves 86 of the shutter curl in a direction out of the page when exposed to excessive temperature, and thereby allow more airflow when exposed to excessive temperature. The shutter 84 can be located between the flame filter 36 as shown, or can be placed below the smoking material 28 (i.e., within the pipe bottom). In an alternative embodiment, the shutter allows air directly from ambient (not through the flame filter), when the temperature is excessive.

Figure 16:
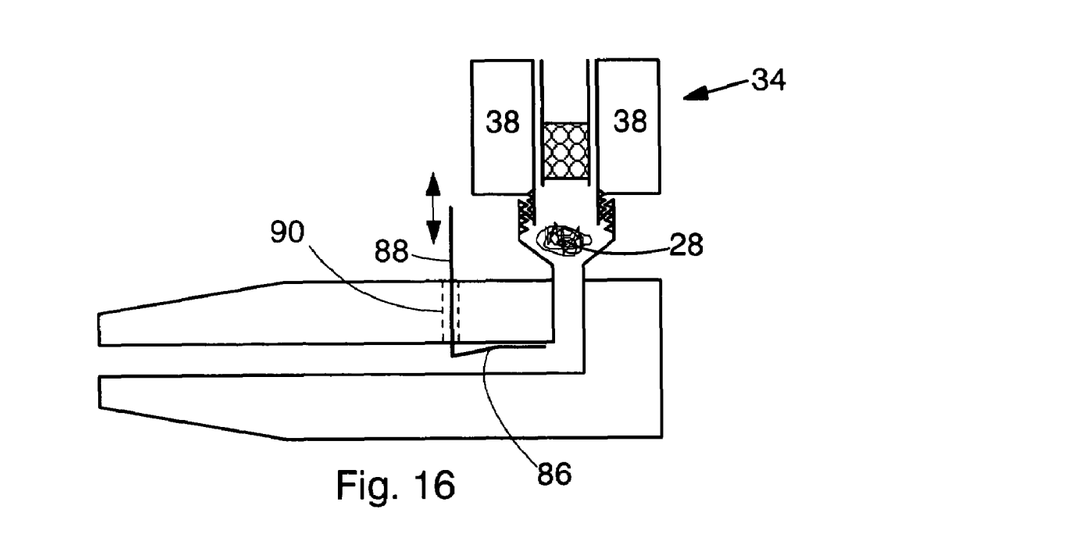
FIG. 16 shows an embodiment having a theromechanical element for indicating temperature inside the device.

FIG. 16 shows yet another embodiment of the invention having a temperature indicator. Specifically, the device has a thermomechanical element (e.g. bimetallic strip) 86 that responds to temperature by raising or lowering a rod 88 through a hole 90. The height of the rod 88 indicates the approximate temperature experienced by the smoking material 28.

Figure 17:
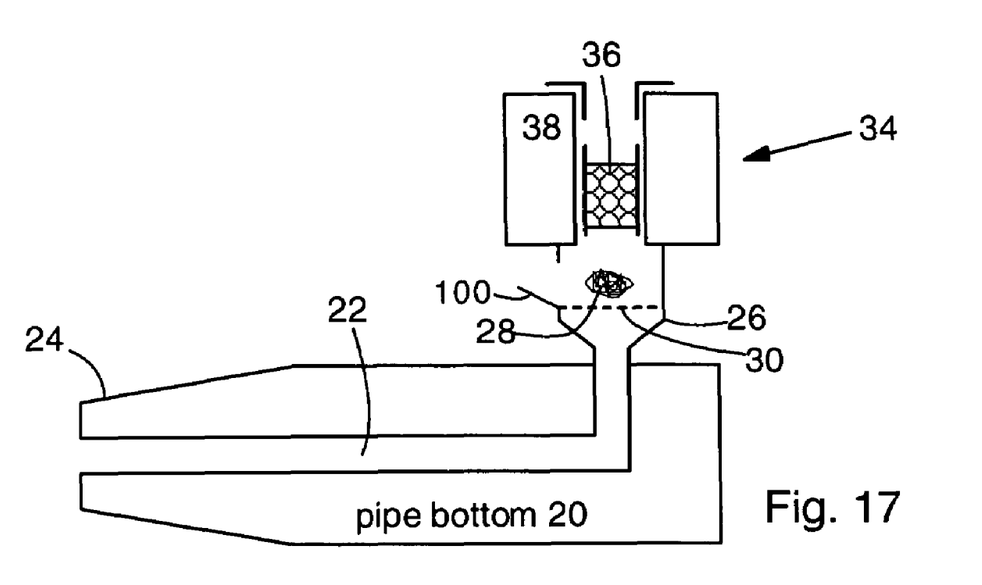
FIG. 17 shows an embodiment where the flame filter is permanently attached to the pip, and the bowl has a door for accessing and inserting the smoking material.

FIG. 17 shows yet another embodiment of the invention where the filter housing 38 is permanently bonded to the bowl. The bowl 26 is provided with a door 100 through which smoking material 28 is loaded into the bowl. The door 100 can open and close. When closed, the door should be air tight, or nearly airtight. In one embodiment, the screen 30 can be withdrawn from the bowl 26 through the door 100 and filled with smoking material 28. Then, the smoking material 28 and screen 30 are loaded into the bowl through the door 100. In the embodiment of FIG. 17, the filter is not removably attachable to the pipe.

Figure 18:
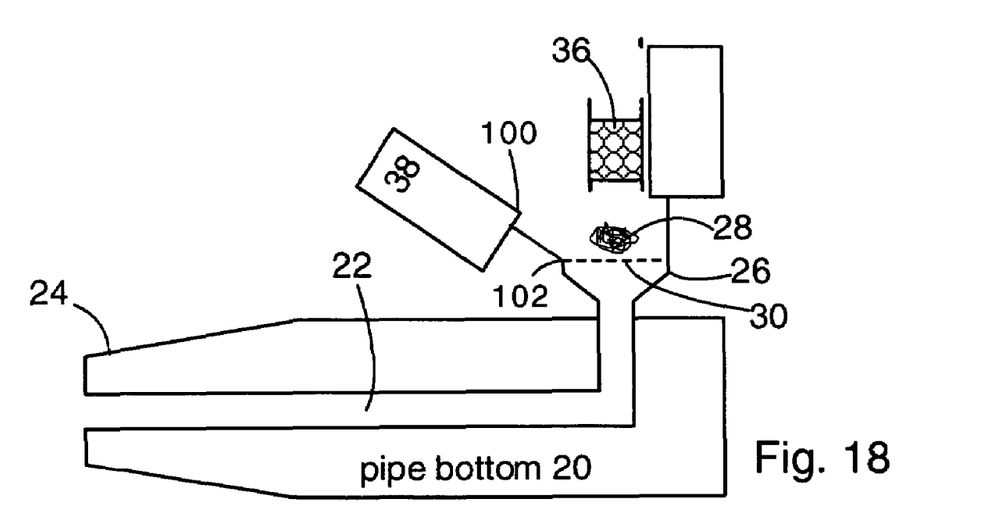
FIG. 18 shows an embodiment where a portion of the filter housing is part of the door.

FIG. 18 shows another embodiment of the invention where a portion of the filter housing 38 and bowl 26 form the door 100 that can be opened to provide access to the smoking material 28. The door 100 pivots on a hinge 102 and is shown in its open position. The flame filter 36 can be attached to the hinged portion of the filter housing, or the stationary portion of the filter housing. In the specific embodiment of FIG. 18, the flame filter 36 is attached to the stationary, unhinged portion of the filter housing.

The present invention is also directed toward only the filter unit, which has a flame filter inside the filter housing, and a means for attaching the filter housing to a pipe. The present filter unit can be used with many different kinds of pipes and devices ordinarily intended for use as conventional smoking devices. In fact, the present filter unit can effectively transform a conventional smoking pipe into a vaporization device. For example, the filter unit can be combined with a water pipe or any other pipe known in the art, and the pipe will act as a vaporizer.

It is also noted that the present invention can be used to produce smoke, if desired. If smoke is desired, a large flame is provided to the flame filter. Smoke produced in the present device will tend to be smoother and more pleasant than smoke produced in a conventional pipe, but will contain the harmful substances known to occur in smoke.

It is noted in the present invention that ceramic materials are generally preferred over metals for use in the flame filter 36. This is because ceramics tend to be much more resistant to oxidation and corrosion at high temperatures. Metals such as brass, copper or bronze tend to oxidize, which produces unhealthful metal oxide particles, which are inhaled. Also, metal flame filters tend to create a metallic taste. Inert metals such as platinum or gold can be used (e.g. as a coating), but such materials are very expensive. Hence, relatively inert ceramics such as silicon carbide, silicon, cordierite, and zirconia are preferred. It is also noted that semiconductor materials such as silicon can be used for the flame filter (e.g. silicon foam), and such materials are understood to fall under the rubric of ceramic materials in the present disclosure. Nevertheless, it is understood that even oxidizable metals (e.g. brass, bronze, steel) will function to provide flame filtering and air mixing, and are therefore included in the present invention and scope of the appended claims.

Also, it is noted that combinations of materials can be used for the flame filter. For example, the flame filter can comprise a screen in combination with a metal or ceramic foam, or a coil of wire in combination with ceramic discs having holes.

The present invention and appended claims require a flame filter having tortured flow paths. A single layer screen does not have flow paths that are tortured. Therefore, a pipe with a single screen is outside the scope of the claims. However, All the embodiments disclosed herein have tortured flow paths and are within the scope of the claims. Specifically, open-cell ceramic foam, a plurality of stacked screens (illustrated in FIG. 6), a web of metal wire (illustrated in FIG. 7), bonded granules, and stacked plates/discs (illustrated in FIGS. 9 and 10) are examples of flame filters having a plurality of tortured flow paths. All of these embodiments are within the scope of the present claims.

It will be clear to one skilled in the art that the above embodiments may be altered in many ways without departing from the scope of the invention. Accordingly, the scope of the invention should be determined by the following claims and their legal equivalents.

What is claimed is:

1. A vaporization device, comprising:
   a) a pipe having:
      1) a bowl for holding smoking material, and
      2) an inhalation end for emitting vapors, wherein the inhalation end is disposed downstream from the bowl;
   b) a heat resistant and porous flame filter, with tortured flow paths, for receiving a flame, wherein the flame filter has a thickness of at least 0.02 inches, and
      wherein the flame filter is disposed upstream from the bowl.

2. The vaporization device of claim 1, wherein the flame filter comprises a material selected from the group consisting of open cell foam, bonded granules, stacked discs, tangled wire, stacked screens, and combinations thereof.

3. The vaporization device of claim 1, wherein the flame filter has a thickness in the range of 0.05-1 inches.

4. The vaporization device of claim 1, wherein the flame filter comprises open-cell foam.

5. The vaporization device of claim 4, wherein the open-cell foam comprises a material selected from the group consisting of silicon, cordierite, oxide-bonded silicon carbide, silicon carbide, CVD silicon, monolithic ceramic, silica-containing ceramics and zirconium-containing ceramics.

6. The vaporization device of claim 1 wherein the flame filter comprises bonded granules.

7. The vaporization device of claim 1 wherein the flame filter has a cross sectional area in the range of 0.015-1 square inches.

8. The vaporization device of claim 1 wherein the flame filter comprises at least two discs with each disc having a least one hole.

9. The vaporization device of claim 1 wherein the flame filter comprises tangled, coiled or folded wire.

10. The vaporization device of claim 1 wherein the flame filter comprises a stack of at least 3 mesh screens.

11. The vaporization device of claim 1 further comprising a filter housing surrounding the flame filter and wherein the filter housing is removably attachable to the pipe.

12. The vaporization pipe of claim 1 wherein the flame filter is made of metal, and the flame filter. has a protective coating.

13. The vaporization device of claim 1 wherein the flame filter is made of material having a thermal conductivity of at least 50 W/mK.

14. The vaporization device of claim 1 further comprising a means for indicating temperature near or within the smoking material.

15. The vaporization device of claim 1 wherein the flame filter is removably attachable to the pipe.

16. The vaporization device of claim 1 wherein the flame filter and bowl are disposed so that an air stream from the flame filter travels straight through the smoking material.

17. A vaporization device, comprising:
   a) a pipe having:
      1) a bowl for holding smoking material, and
      2) an inhalation end for emitting vapors, wherein the inhalation end is disposed downstream from the bowl;
   b) a heat resistant flame filter for receiving a flame, wherein the flame filter is made of open-cell ceramic foam, and wherein the flame filter is disposed upstream from the bowl.

18. The vaporization pipe of claim 17 wherein the flame filter is made of silicon carbide ceramic foam.

19. The vaporization pipe of claim 17 wherein the flame filter has a thickness of at least 0.02 inches.

20. The vaporization pipe of claim 17 wherein the flame filter has a thickness in the range of 0.05 to 1 inches.

21. The vaporization pipe of claim 17 wherein the ceramic foam has PPI rating in the range of 40-120, inclusive.

22. The vaporization device of claim 17 wherein an air stream from the flame filter travels straight through the smoking material.

23. The vaporization device of claim 17 further comprising a filter housing surrounding the flame filter and wherein the filter housing is removably attachable to the pipe.

24. The vaporization device of claim 17 wherein the flame filter is removably attachable to the pipe.

25. A vaporization device, comprising:
   a) a pipe having:
      1) a bowl for holding smoking material, and
      2) an inhalation end for emitting vapors, wherein the inhalation end is disposed downstream from the bowl;
   b) a heat resistant and porous flame filter for receiving a flame, wherein the flame filter has a thickness of at least 0.02 inches, wherein the flame filter is disposed upstream from the bowl, and wherein the flame filter comprises a material selected from the group consisting of open cell foam, bonded granules, stacked discs, tangled wire, stacked screens, and combinations thereof.

26. The vaporization pipe of claim 25 wherein the flame filter has a thickness in the range of 0.1 to 0.75 inches.

27. The vaporization pipe of claim 25 wherein the open-cell foam is monolithic silicon carbide ceramic foam.

28. A filter unit for attachment to a pipe having a bowl for holding smoking material, and having an inhalation end for emitting vapors, wherein the inhalation end is disposed downstream from the bowl, the filter unit comprising:
   a) a filter housing;
   b) a heat resistant and porous flame filter disposed in the filter housing, wherein the flame filter has a thickness of at least 0.02 inches, and wherein the flame filter comprises a material selected from the group consisting of open cell foam, bonded granules, stacked discs, tangled wire, stacked screens, and combinations thereof,
   c) a means for attaching the filter housing to the pipe such that the flame filter is disposed upstream from the bowl.

29. The filter unit of claim 28 wherein the flame filter comprises open-cell ceramic foam.

30. The filter unit of claim 28 wherein the flame filter comprises silicon carbide ceramic foam.

31. The vaporization device of claim 1, wherein the flame filter has a combustion catalytic coating.

32. The filter unit of claim 28 wherein the flame filter has a thickness in the range of 0.05 to 0.75 inches.

* * * * *

(12) EX PARTE REEXAMINATION CERTIFICATE (9100th)
United States Patent
Steinberg (10) Number: US 7,434,584 C1
(45) Certificate Issued: Jun. 26, 2012

(54) VAPORIZATION PIPE WITH FLAME FILTER

(75) Inventor: Dan Steinberg, Blacksburg, VA (US)

(73) Assignee: Vaporgenie LLC, Blacksburg, VA (US)

Reexamination Request:
No. 90/009,529, Dec. 10, 2009

Reexamination Certificate for:
Patent No.: 7,434,584
Issued: Oct. 14, 2008
Appl. No.: 10/639,344
Filed: Aug. 12, 2003

Related U.S. Application Data (63) Continuation-in-part of application No. 10/318,877, filed on Dec. 13, 2002, now abandoned.
(60) Provisional application No. 60/429,120, filed on Nov. 26, 2002, provisional application No. 60/399,465, filed on Jul. 29, 2002, provisional application No. 60/384,551, filed on May 29, 2002, and provisional application No. 60/366,809, filed on Mar. 22, 2002.

(51) Int. Cl.
| | |
|---|---|
| *F23D 14/02* | (2006.01) |
| *A24F 13/12* | (2006.01) |
| *A24F 47/00* | (2006.01) |
| *F23Q 2/16* | (2006.01) |
| *F23Q 2/28* | (2006.01) |
| *F23Q 2/32* | (2006.01) |
| *F23Q 7/00* | (2006.01) |

(52) U.S. Cl. .................. 131/194; 131/185; 131/329; 131/351; 431/253; 431/268
(58) Field of Classification Search .................. 131/194
See application file for complete search history.

(56) References Cited

To view the complete listing of prior art documents cited during the proceeding for Reexamination Control Number 90/009,529, please refer to the USPTO's public Patent Application Information Retrieval (PAIR) system under the Display References tab.

*Primary Examiner* — Carlos Lopez (57) ABSTRACT

A vaporizer device that uses a flame for vaporizing flavor and psychoactive compounds from smoking materials such as tobacco. The present device has a filter unit 34 with a porous flame filter 36. The flame filter 36 can be made of open-cell ceramic or metal foam, sintered ceramic or metal granules or other porous, heat resistant materials. In use, flame is supplied to the flame filter, and inhalation causes ambient air to enter the flame filter as well. The flame exhaust and ambient air are mixed within the flame filter and produce an air stream of intermediate temperature. The intermediate temperature air stream is hot enough to vaporize desirable components from the smoking material, but generally is not hot enough to burn the smoking material. The temperature of the air stream can be controlled by adjusting the amount of flame supplied to the flame filter 36.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 17, 25 and 28 are cancelled.

New claims 33-48 are added and determined to be patentable.

Claims 2-16, 18-24, 26-27, 29-32 were not reexamined.

33. *A vaporization device, comprising:*
   *1) a bowl for holding smoking material,*
   *2) an inhalation end for emitting vapors and for contact with the user's mouth, wherein the inhalation end is fluidically connected to the bowl downstream from the bowl, and*
   *3) a heat resistant and porous flame filter with tortured flow paths, for receiving a flame;*
   *wherein the flame filter has a thickness of at least 0.02 inches, and wherein the flame filter is fluidically connected to the bowl upstream from the bowl.*

34. *A vaporization device, comprising:*
   *1) a bowl for holding smoking material, and*
   *2) an inhalation end for emitting vapors and for contact with a user's mouth, wherein the inhalation end is fluidically connected to the bowl downstream from the bowl;*
   *3) a heat resistant flame filter for receiving a flame, wherein the flame filter is made of open-cell ceramic foam, and wherein the flame filter is fluidically connected to the bowl upstream from the bowl.*

35. *A vaporization device, comprising:*
   *1) a bowl for holding smoking material, and*
   *2) an inhalation end for emitting vapors, wherein the inhalation end is fluidically connected to the bowl downstream from the bowl;*
   *3) a filter housing fluidically connected to the bowl upstream from the bowl, wherein the filter housing is removably attachable to the bowl;*
   *4) a heat resistant and porous flame filter disposed in the filter housing, wherein the flame filter has a thickness of at least 0.02 inches, wherein the flame filter is fluidically connected to the bowl upstream from the bowl, and wherein the flame filter comprises a material selected from the group consisting of open cell foam, bonded granules, stacked discs, tangled wire, stacked screens, and combinations thereof.*

36. *A filter unit for attachment to a pipe having a bowl for holding smoking material, and having an inhalation end for emitting vapors, wherein the inhalation end is fluidically connected to the bowl downstream from the bowl, the filter unit comprising:*
   *a) a filter housing having input and output orifices that are fluidically connected;*
   *b) a heat resistant and porous flame filter disposed in the filter housing between input and output orifices, wherein the flame filter has a thickness of at least 0.02 inches; and wherein the flame filter comprises a material selected from the group consisting of open cell foam, bonded granules, stacked discs, tangled wire, stacked screens, and combinations thereof;*
   *c) a means for removably attaching the filter housing to the pipe such that the flame filter and output orifice are fluidically connected to the bowl upstream from the bowl.*

37. *A vaporization device, comprising:*
   *1) a bowl for holding smoking material;*
   *2) an inhalation end, wherein the inhalation end is fluidically connected to the bowl downstream from the bowl;*
   *3) a filter housing fluidically connected to the bowl upstream from the bowl;*
   *4) a flame filter comprising open cell metal or ceramic foam, disposed in the filter housing and fluidically connected to the bowl, wherein there is no air intake orifice between the flame filter and the bowl.*

38. *The vaporization device of claim 37 wherein flame exhaust and ambient air enter the filter on a same surface of the filter.*

39. *The vaporization device of claim 37 wherein the filter housing is removably attachable to the bowl.*

40. *The vaporization device of claim 37 wherein the flame filter is made of silicon carbide ceramic foam.*

41. *The vaporization device of claim 36 wherein the means for removably attaching the filter housing comprises screw threads.*

42. *The vaporization device of claim 33 wherein flame exhaust and ambient air enter the filter on a same surface of the filter.*

43. *The vaporization device of claim 34 wherein flame exhaust and ambient air enter the filter on a same surface of the filter.*

44. *The vaporization device of claim 35 wherein flame exhaust and ambient air enter the filter on a same surface of the filter.*

45. *The filter unit of claim 36 wherein flame exhaust and ambient air enter the filter on a same surface of the filter.*

46. *The vaporization device of claim 33 wherein there is no air intake orifice between the flame filter and the bowl.*

47. *The vaporization device of claim 34 wherein there is no air intake orifice between the flame filter and the bowl.*

48. *The vaporization device of claim 35 wherein there is no air intake orifice between the flame filter and the bowl.*

\* \* \* \* \*